United States Patent [19]

Duranleau et al.

[11] 4,089,867

[45] May 16, 1978

[54] PREPARATION OF DIACYLFURAZAN OXIDES

[75] Inventors: Roger G. Duranleau, Bridge City; John M. Larkin, Austin, both of Tex.; Stanley R. Newman, Fishkill, N.Y.

[73] Assignee: Texaco Inc., New York, N.Y.

[21] Appl. No.: 740,997

[22] Filed: Nov. 11, 1976

[51] Int. Cl.$^2$ .............................. C07D 271/08
[52] U.S. Cl. ......................... 260/307 G; 260/566 A; 260/590 R; 260/593 R; 423/DIG. 14
[58] Field of Search ..................... 260/307 G

[56] References Cited

PUBLICATIONS

Wiley—"Chemistry of Heterocyclic Compounds"—vol. 17, (1962)–Interscience Publishers—p. 302.
Snyder et al.—J.A.C.S. 77, 4233–4237 (1955).
Fieser et al.—"Reagents for Organic Synthesis" John Wiley & Sons (1967)–pp. 1172, 1175–1176.

*Primary Examiner*—Raymond V. Rush
*Attorney, Agent, or Firm*—Thomas H. Whaley; Carl G. Ries; George J. Darsa

[57] ABSTRACT

Diacylfurazan oxides are prepared by catalytic dimerization of alpha-nitroketones.

16 Claims, No Drawings

PREPARATION OF DIACYLFURAZAN OXIDES

BACKGROUND OF THE INVENTION

This invention relates to a novel method of preparing diacylfurazan oxides from alpha-nitroketones. In particular, it relates to a method for preparing diacylfurazan oxides by catalytic dimerization of alpha-nitroketones.

Diacetylfuroxan has been prepared by oxidizing acetone with nitrogen tetroxide at 0°–5° C. and thereafter heating the initial reaction product to 50° C. as described in Peterson, Tet. Letters, 16 1727 (1966). While such a two-step method provided a high yield of diacetylfuroxan, the initial step provides a highly unstable intermediate. An attempt to distill the crude reaction product of the initial step which contained substantial amounts of this unstable intermediate was reported to have resulted in an explosion. The aforementioned disadvantage seriously detracts from the attractiveness of such processes. A method has now been found whereby diacylfurazan oxides can be produced in good yields and where the threat of explosion is substantially reduced.

It is therefore an object of this invention to provide a novel method for the preparation of diacylfurazan oxides.

It is another object of this invention to provide a catalytic method for the preparation of diacylfurazan oxides.

Yet another object of this invention is to provide a method for preparing diacylfurazan oxides from alpha-nitroketones in a single step.

Other objects and advantages will become apparent from a reading of the following detailed description and examples.

SUMMARY OF THE INVENTION

Broadly, this invention contemplates a method for the preparation of diacylfurazan oxides which comprises dimerizing an alpha-nitroketone in the presence of catalytic amounts of an organic acid having a $pk_a$ of about 4.0 to about 0.5.

According to our invention, the alpha-nitroketones dimerized to diacylfurazan oxides by the instant method correspond to the formula:

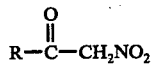

where R is an alkyl group having from 1 to 20 carbon atoms or an aryl group of from 6 to 20 carbon atoms. Illustrative of the alpha-nitroketones contemplated herein can be mentioned 1-nitro-2-propanone, 1-nitro-2-butanone, 1-nitro-2-pentanone, 1-nitro-2-hexanone, 1-nitro-2-heptanone, 1-nitro-2-octanone, 1-nitro-2-decanone, 1-nitro-2-dodecanone, 1-nitro-2-pentadecanone, 1-nitro-2-hexadecanone, 1-nitro-2-heptadecanone, 1-nitro-2-eicosanone, 1-nitro-2-heneicosanone, omega-nitroacetophenone, 4'-tertbutyl-2-nitroacetophenone, 2'-methyl-2-nitroacetophenone and omega-nitroacetonaphthone. Internal nitroketones, that is, nitroketones where the nitro group is on other than a terminal carbon, do not react in the instant method to produce the desired diacylfurazan oxides.

More specifically, the method of this invention comprises catalytically dimerizing the nitroketone or mixtures of nitroketones as hereinabove described at temperatures of from about 50° to 150° C., preferably from about 80° to 110° C. in the presence of a catalyst. The catalysts contemplated in the instant method are organic acids having a $pk_a$ of about 4.0 to about 0.5, preferably about 2.0 to 0.5. In general, the organic acids have 2 to 18 carbons. Illustrative of the organic acids we mention organic sulfonic acids of 6 to 18 carbons such as p-toluenesulfonic acid, m-toluenesulfonic acid, p-bromobenzenesulfonic acid, p-chlorobenzenesulfonic acid, 2,6-naphthalenedisulfonic acid, 1-naphthalenesulfonic acid, 2-naphthalenesulfonic acid, benzenesulfonic acid, 2-mesitylenesulfonic acid and 2-dodecylphenylsulfonic acid; aromatic nitro acids of 7 to 11 carbons such as p-nitrobenzoic acid, m-nitrobenzoic acid, 2-methyl-4-nitrobenzoic acid, 2-butyl-4-nitrobenzoic acid and p-nitrophenylacetic acid; and alpha-halogenated alkanoic acids of 2 to 5 carbons such as chloroacetic acid, dichloroacetic acid, trichloroacetic acid, dichloropropanoic acid and dichlorobutanoic acid. The preferred catalysts are the organic sulfonic acids, particularly p-toluenesulfonic acid. The use of inorganic acids such as sulfuric acid or hydrochloric acid are excluded from the present method in view of their poor miscibility in the reaction and the introduction of water by such aqueous inorganic acids is deleterious to the dimerization reaction.

The catalytic reaction is suitably conducted in the presence of a non-reactive, non-polar organic solvent illustrated by benzene, toluene, xylene, chlorobenzene, carbon tetrachloride, hexane, heptane, cyclohexane, cycloheptane, 2,2,4-trimethylpentane, decane, dodecane, decalin, tetralin, and the like. Typically, the solvent has a boiling point of between about 70° and 250° C. Highly preferred solvents are benzene and toluene. The use of a polar solvent such as alcohols or low molecular weight carboxylic acids is deleterious to the method in that polar solvents are reactive with the nitroketone and lead to the formation of, for example, esters or amides. The reaction should also be conducted in an essentially non-aqueous environment, that is, in the substantial absence of added water. The reaction described herein is sensitive to water and water introduced in amounts exceeding about 0.1 weight percent based on the weight of the nitroketone promote competing reactions and the formation of acids and amides instead of the desired products. Moreover, water is a by-product of the instant catalytic reaction and it is preferred to separate the water produced during the reaction as soon as practicable. For example, when a batch catalytic reaction is conducted, the water formed can be continuously removed from the reaction zone by, for example, conducting the method under partial refluxing conditions and at atmospheric pressure with continuous slow distillation of the reaction solvent. In continuous operations, as when the nitroketone and catalyst are continuously contacted and passed through a reaction zone, the water produced can be separated by distillation. The diacylfurazan oxide product in high purity can be recovered by initially contacting the reaction mixture with an aqueous alkaline solution, such as aqueous sodium bicarbonate, at below the reaction temperature, typically at about room temperature, thereby neutralizing the acid catalyst. After separating the aqueous layer containing the neutralized catalyst, the organic layer composed of solvent, product and unconverted nitroketone can be distilled to separate the solvent. The purity of the recovered product can be further improved by recrystallization employing a solvent wherein the nitroketone is soluble but where the product is insoluble, as for example, acetic acid.

The catalytic method described above provides diacylfurazan oxides corresponding to the formula:

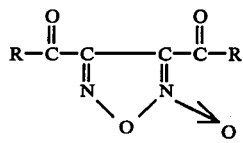

where R is as defined above. It will be understood that R can represent identical groups as in those instances where a single nitroketone is used in the method or different groups as when mixtures of nitroketones, such as mixtures of nitroalkanones of varying molecular weight, such as mixtures of $C_3$ and $C_4$ or $C_{10}$ to $C_{14}$ nitroketones, mixtures of nitroacetophenones or mixtures of nitroalkanones and nitroacetophenones are employed. The term diacylfurazan oxides is intended to include dialkanoylfurazan oxides, diaroylfurazan oxides and alkanoyl-aroylfurazan oxides. Illustrative of the diacylfurazan oxides provided by the method we mention 3,4-diethanoylfurazan oxide, 3,4-dipropanoylfurazan oxide, 3,4-dibutanoylfurazan oxide, 3,4-dipentanoylfurazan oxide, 3,4-dihexanoylfurazan oxide, 3,4-dioctanoylfurazan oxide, 3,4-diundecanoylfurazan oxide, 3,4-dipentanoylfurazan oxide, 3,4-dieicosanoylfurazan oxide, 3,4-dibenzoylfurazan oxide, 3,4-di-2-methylbenzoylfurazan oxide, 3,4-di-1-naphthanoylfurazan oxide, 3,4-di-4-tertiarybutylbenzoylfurazan oxide, 3-pentanoyl-4-octanoylfurazan oxide, 3-hexanoyl-4-benzoylfurazan oxide and 3-benzoyl-4-pentadecanoylfurazan oxide. The diacylfurazan oxides provided herein are useful, for example, in preparing polyoxime ester polymers related to those described in U.S. Pat. No. 3,026,303. The diacylfurazan oxides can be reduced to diacyldioximes, illustratively 3,4-diethanoylfurazan oxide reduced to diethanoylglyoxime, employing a reducing agent such as zinc in acetic acid or stannous chloride. The diacyldioxime can be reacted with a dibasic acid, such as succinic acid, adipic acid, sebacic acid or terephthalic acid, or a dibasic fatty acid chloride, such as succinyl acid chloride, adipyl acid chloride or sebacyl acid chloride, to provide a polydiacylglyoxime ester useful as molding powders, casting resins or pigments. Diacyldioximes can also be utilized as chelating agents for transition metals such as nickel. Nickel chelates can be formed and removed from copper leaching solutions as, for example, in copper mining.

In order to more fully illustrate the nature of our invention and the manner of practicing the same, the following examples are presented.

EXAMPLE 1

A solution of 1-nitro-2-hexadecanone (12.80 grams, 0.045 mole) in toluene (112 milliliters) and p-toluenesulfonic acid (1.43 grams, 0.0075 mole) was refluxed for 160 minutes and samples (25 milliliters) were taken at twenty minute intervals at 20, 40, 60 and 80 minutes. Water was collected in a trap as soon as refluxing began. The 60 minute sample was evaporated to dryness at 80° C. and 15 mm Hg. and infrared analysis thereof indicated nearly complete conversion of the nitroketone (greater than 97%). Infrared spectrum and nuclear magnetic resonance analyses identified the product as 3,4-dipentadecanoylfurazan oxide.

EXAMPLE 2

Example 1 was repreated using double the amounts of 1-nitro-2-tetradecanone and p-toluenesulfonic acid in 196 milliliters of benzene. The entire product was recovered by evaporation of the solvent at 30° C. and 15 mm Hg. The evaporation residue afforded 21.55 grams of product (92 percent yield). The product was recrystallized from glacial acetic acid and 15.2 grams of product having a melting point of 50°–55° C. was recovered. Elemental and mass spectrum analyses identified the product as 3,4-ditridecanoylfurazan oxide.

EXAMPLE 3

In the manner described in Example 1, 3,4-dipentadecanoylfurazan oxide is prepared except that p-bromobenzenesulfonic acid (1.78 gram, 0.0076 mole) is substituted for p-toluenesulfonic acid.

EXAMPLE 4

Following the preocedure of Example 1, 3,4-dipentadecanoylfurazan oxide is prepared except that 4-nitrobenzoic acid (1.52 gram, 0.0075 mole) is substituted for p-toluenesulfonic acid.

EXAMPLE 5

3,4-dioctanoylfurazan oxide is prepared by forming a solution of 1-nitro-2-nonanone (17.3 grams, 0.1 mole) in 125 milliliters of m-xylene and 0.175 gram (0.001 mole) of m-toluenesulfonic acid, heating to 120° C. for 160 minutes and separating water from the reaction. The product is recovered by evaporation of the solvent at 80° C. and 15 mm Hg.

EXAMPLE 6

In the manner described in Example 5, 3,4-dioctanoylfurazan oxide is prepared except that 0.20 gram (0.001 mole) of chlorobenzenesulfonic acid is used as the catalyst.

We claim:
1. A method for the preparation of diacylfurazan oxides corresponding to the formula:

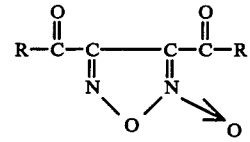

where R is an alkyl group having 1 to 20 carbon atoms or an aryl group of 6 to 20 carbon atoms which comprises contacting an alpha-nitroketone or a mixture of alpha-nitroketones of the formula:

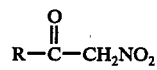

where R is as defined above with catalytic amounts of an organic acid having 2 to 18 carbon atoms and a $pk_a$ of about 4.0 to about 0.5 in the substantial absence of added water and in the presence of a non-reactive, non-polar solvent at a temperature of from about 50° to 150° C.

2. A method according to claim 1 wherein said contacting is conducted at a temperature of from about 80° to 110° C.

3. A method according to claim 1 wherein said nitroketone is 1-nitro-2-hexadecanone.

4. A method according to claim 1 wherein said nitroketone is 1-nitro-2-tetradecanone.

5. A method according to claim 1 wherein said nitroketone is 1-nitro-2-decanone.

6. A method according to claim 1 wherein said nitroketone is omega-nitroacetophenone.

7. A method for the preparation of diacylfurazan oxides corresponding to the formula:

$$R-\overset{O}{\underset{\|}{C}}-CH_2NO_2$$

where R is an alkyl group having 1 to 20 carbon atoms or an aryl group of 6 to 20 carbon atoms which comprises contacting an alpha-nitroketone or a mixture of alpha-nitroketones of the formula:

$$R-\overset{O}{\underset{\|}{C}}-CH_2NO_2$$

where R is as defined above with catalytic amounts of an organic acid having a pk$_a$ of about 4.0 to about 0.5 wherein said acid is an alpha-halogenated alkanoic acid of 2 to 5 carbon atoms in the substantial absence of added water and in the presence of a non-reactive, non-polar solvent at a temperature of from about 50° to 150° C.

8. A method for the preparation of diacylfurazan oxides corresponding to the formula:

[structure of diacylfurazan oxide with R-C(=O)-C=N-O-N=C-C(=O)-R and N-oxide]

where R is an alkyl group having 1 to 20 carbon atoms or an aryl group of 6 to 20 carbon atoms which comprises contacting an alpha-nitroketone or a mixture of alpha-nitroketones of the formula:

$$R-\overset{O}{\underset{\|}{C}}-CH_2NO_2$$

where R is as defined above with catalytic amounts of an organic acid having a pk$_a$ of about 4.0 to about 0.5 wherein said acid is an aromatic nitro acid of 7 to 11 carbon atoms in the substantial absence of added water and in the presence of a non-reactive, non-polar solvent at a temperature of from about 50° to 150° C.

9. A method for the preparation of diacylfurazan oxides corresponding to the formula:

[structure of diacylfurazan oxide]

where R is an alkyl group having 1 to 20 carbon atoms or an aryl group of 6 to 20 carbon atoms which comprises contacting an alpha-nitroketone or a mixture of alpha-nitroketones of the formula:

$$R-\overset{O}{\underset{\|}{C}}-CH_2NO_2$$

where R is as defined above with catalytic amounts of an organic acid having a pk$_a$ of about 4.0 to about 0.5 wherein said acid is an organic sulfonic acid of 6 to 18 carbon atoms in the substantial absence of added water and in the presence of a non-reactive, non-polar solvent at a temperature of from about 50° to 150° C.

10. A method according to claim 1 wherein said acid is p-toluenesulfonic acid.

11. A method according to claim 1 wherein said solvent is toluene.

12. A method according to claim 1 wherein said solvent is benzene.

13. A method according to claim 1 wherein byproduct water is continuously separated from the reaction.

14. A method according to claim 1 wherein said furazan oxide is 3,4-dioctanoylfurazan oxide.

15. A method for the preparation of diacylfurazan oxides corresponding to the formula:

[structure of diacylfurazan oxide]

where R is an alkyl group having 1 to 20 carbon atoms which comprises contacting an alpha-nitroketone or a mixture of alpha-nitroketones of the formula:

$$R-\overset{O}{\underset{\|}{C}}-CH_2NO_2$$

where R is as defined above with catalytic amounts of an organic acid having 2 to 18 carbon atoms and a pk$_a$ of about 4.0 to about 0.5 in the substantial absence of added water and in the presence of a non-reactive, non-polar solvent at a temperature of from about 50° to 150° C.

16. A method according to claim 15 wherein said furazan oxide is 3,4-dipentadecanoylfurazan oxide.

* * * * *

UNITED STATES PATENT AND TRADEMARK OFFICE
CERTIFICATE OF CORRECTION

PATENT NO. : 4,089,867
DATED : 9/13/78
INVENTOR(S) : ROGER G. DURANLEAU ET AL.

It is certified that error appears in the above–identified patent and that said Letters Patent are hereby corrected as shown below:

Column 5, lines 13-15, the formula should read and appear as follows:

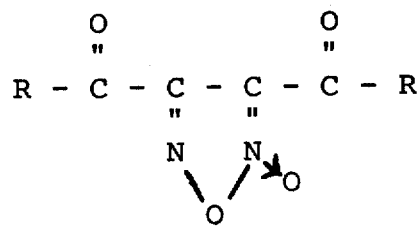

Signed and Sealed this

Thirty-first Day of October 1978

[SEAL]

Attest:

RUTH C. MASON
Attesting Officer

DONALD W. BANNER
Commissioner of Patents and Trademarks